May 19, 1953 M. TANTAU Plant Pat. 1,189
ROSE PLANT
Filed June 5, 1952
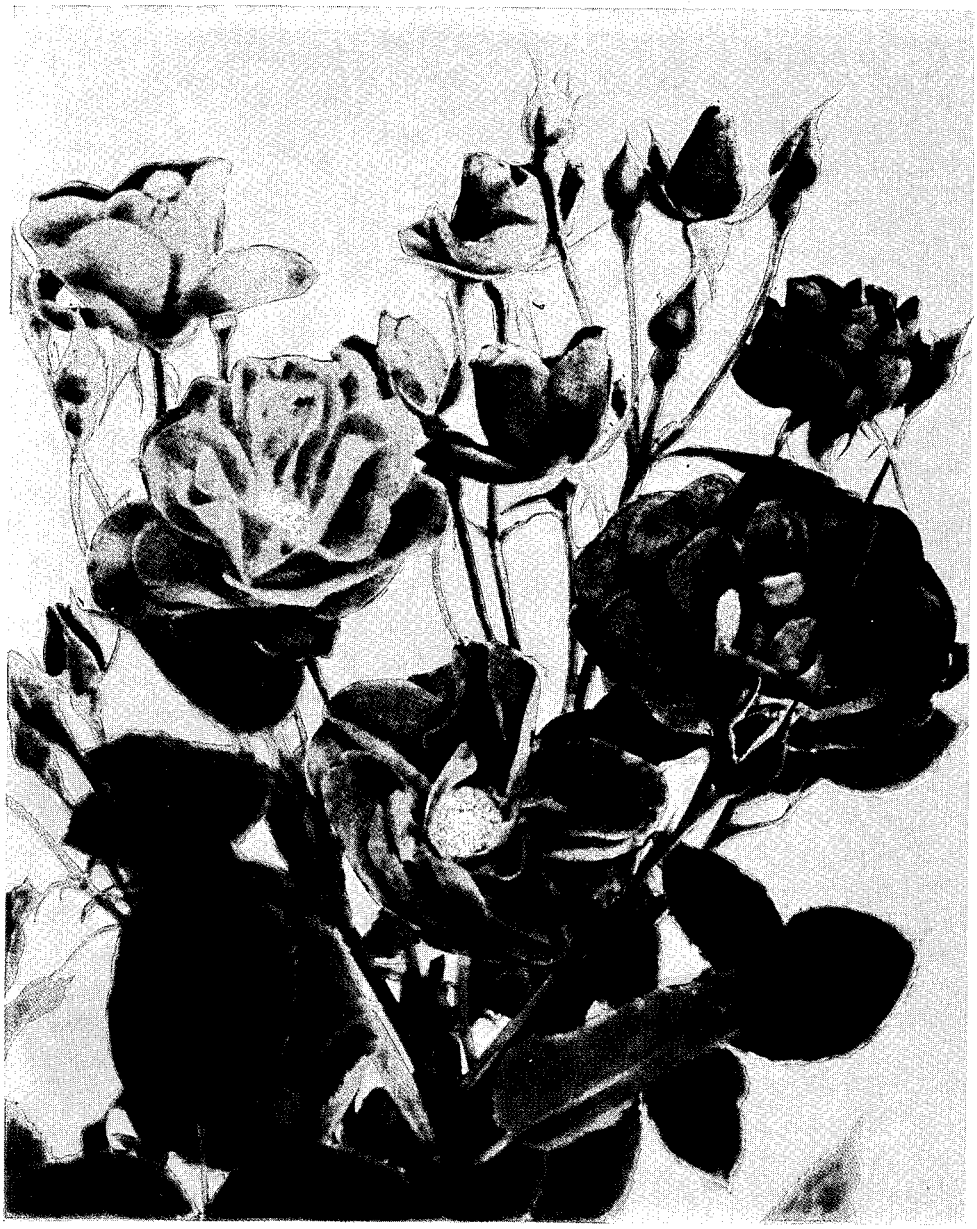
Inventor.
Mathias Tantau
By: Cobb & Cobb
Attorneys.

Patented May 19, 1953

Plant Pat. 1,189

UNITED STATES PATENT OFFICE 1,189

ROSE PLANT

Mathias Tantau, Uetersen, Germany, assignor to The Conard-Pyle Company, West Grove, Pa., a corporation of Pennsylvania Application June 5, 1952, Serial No. 292,014

1 Claim. (Cl. 47—61)

The present invention relates to a new and distinct variety of rose plant of the large-flowered hybrid polyantha class, now commonly termed "floribunda" in the United States, originated by me by crossing the variety "Karl Weinhausen" (unpatented) with the variety "Cinnabar," sometimes known as "Tantau's Triumph" (unpatented).

This new variety constitutes a marked advance, to date, in the development of this comparatively new class of roses, the advance being represented by a unique combination of characteristics which distinguish this variety from its parents, as well as from all other varieties of its class.

More particularly, my new variety is characterized by the following outstanding features:

(1) An unusually velvety petal texture for roses of this class;

(2) A fixed and long-lasting deep red color that, as illustrated in the accompanying drawing and hereinafter described in more detail, remains virtually unchanged from the early bud through successive stages of bloom, and endures even despite adverse weather conditions;

(3) The long persistence of the blooms without petal deterioration;

(4) The regularity of form of its clusters of inflorescence, and the way these are evenly produced on the plant; and (5) The upright, compact and even growth which give this variety an extended value as a border or hedge plant, as well as for cut flowers and for other forms of garden decoration.

Asexual reproduction of my new variety by buddings both at Uetersen (Holstein) Germany, and at West Grove, Pennsylvania, U. S. A., shows that the foregoing characteristics come true to form and are established and transmitted through succeeding propagations.

The accompanying drawing shows specimens of my new variety, with the flowers and foliage illustrated in different stages of development, and with the colors depicted as nearly true as it is reasonably possible to make the same in an illustration of this character.

The following is a detailed description of my new variety, with color terminology in accordance with Ridgway's Color Standards and Nomenclature, except where general color terms of ordinary dictionary significance are obvious:

Type: Hardy; bush; outdoor; for cut flowers and for garden decoration.

Class: Hybrid polyantha.

Breeding: Seedling.

*Seed parent.*—"Karl Weinhausen."

*Pollen parent.*—"Cinnabar."

Propagation: Holds its distinguishing characteristics through succeeding propagations by budding.

*Flower*

Locality where grown and observed: West Grove, Pennsylvania, U. S. A.

Flowers borne: Several to stem; in regular cluster; on normal, strong, medium length stems.

Quantity of bloom: Free to abundant.

Continuity: Continuous; continues well even after frost in fall.

Fragrance: Slight to moderate; tea.

Bud:

*Peduncle.*—Medium length; medium caliper; erect; rough; medium number of reddish prickles.

*Before calyx breaks.*—Size—medium. Form—medium length; ovoid; with foliaceous appendages on the surface of the bud; with little cut foliaceous parts extending beyond the tip of the bud equal to one-fourth or more of its length.

*As calyx breaks.*—Color—Dark Oxblood Red, Plate I.

*As first petal opens.*—Size—medium. Form—medium length. Color—Outside—Dark Oxblood Red, Plate I; small area of yellowish white at base. Inside—Dark Oxblood Red, Plate I; small area of yellowish white at base.

*Opening.*—Opens up well.

Bloom:

*Size, when fully open.*—Medium; 2½ inches to 2¾ inches.

*Petalage.*—Semi-double; from 12 to 14 petals; arranged regularly.

*Form.*—Cupped at first; becoming flat; petals being at first cupped inward; becoming later at maturity flat.

Petals: Thick; with inside velvety and outside somewhat shiny.

*Shape.*—Outer—obovate to obcordate; sometimes with a small point at apex. Intermediate—obovate to obcordate; sometimes with a small point at apex. Inner—obovate to obcordate; sometimes with a small point at apex.

This description of a newly opened flower was made from a rose grown outdoors in the month of October, at West Grove, Pennsylvania, U. S. A.:

*Color.*—Outer petal—outside surface: Light Oxblood Red, Plate I; inside surface: Oxblood Red, Plate I. Intermediate petal—outside surface: Light Oxblood Red, Plate I; inside surface: Velvety Oxblood Red, Plate I. Inner petal—outside surface: Carmine, Plate I; inside surface: Velvety Oxblood Red, Plate I.

This description was made from a rose that was open for three days outdoors in the month of October, at West Grove, Pennsylvania, U. S. A.:

*Color.*—Outer petal—outside surface: Dark Carmine, Plate I; inside surface: Velvety Dark Carmine, Plate I, to Oxblood Red, Plate I. Inner petal—outside surface: Velvety Oxblood Red, Plate I; inside surface: Velvety Carmine, Plate I.

*General color effect.*—Newly opened flower—Velvety Oxblood Red, Plate I. Three days open—Velvety Carmine, Plate I.

*Behavior.*—Drop off cleanly.

*Flower longevity.*—Cut roses grown outdoors kept at living-room temperatures—4 to 5 days in October.

*Reproductive organs*

Stamens: Medium number; arranged regularly about pistils.

Filaments: Most with anthers; short to medium length. Color—Yellowish White to Rose Color, Plate XII.

Anthers: All open at once; small; occasionally an anther fused with a petaloid. Color—Light Cadmium, Plate IV.

Pollen: Moderate. Color—Light Cadmium, Plate IV.

Pistils: Medium number.

Styles: Fairly even; medium short; medium caliper; bunched.

Stigma: Color—greenish white.

Ovaries: All enclosed in calyx.

Hips: Medium length; globular; smooth; walls medium thickness. Color—Apple Green, Plate XVII, to Calliste Green, Plate VI; later becoming Flame Scarlet, Plate II.

Sepals: Permanent while petals remain; falling after hips form; medium length; spear-shaped.

Seeds: Medium number; medium size.

*Plant*

Foliage:

*Leaves.*—Compound of three to five leaflets; abundant; medium size; leathery; glossy.

*Leaflets.*—Shape—almost oval, with apex acute. Base—obtuse. Margin—simply serrate.

*Color.*—Mature—upper surface: Light Cress Green, Plate XXXI; under surface: dark Cress Green, Plate XXXI. Young—upper surface: Reddish Cameo Brown, Plate XXVIII; under surface: Deep Corinthian Red, Plate XXVII.

*Rachis.*—Medium caliper. Upper side—grooved. Under side—sparsely prickly and thorny.

*Stipules.*—Medium length; medium width; with medium length points turning out at an angle of less than 90°.

*Disease.*—Resistant to mildew and blackspot, as determined by comparison with other varieties grown under comparable conditions.

Growth:

*Habit.*—Bushy; upright; branched.

*Growth.*—Free.

*Canes.*—Heavy.

*Main Stems.*—Color—Light Yew Green, Plate XXXI. Thorns—medium length; many; hooked downward; with medium length oval base; with incipient thorns among large thorns. Prickles—none. Hairs—none.

*Branches.*—Color—Jade Green, Plate XXXI. Thorns—several; medium length; hooked downward; with medium length oval base; with a few incipient thorns among the large thorns. Prickles—none. Hairs—none.

*New shoots.*—Color—Yellowish Oil Green, Plate V, often tinged with Pompeian Red, Plate XIII. Thorns—few; medium length; hooked downward; with medium length oval base. Prickles—none. Hairs none.

I claim:

A new and distinct variety of rose plant of the large-flowered, hybrid polyantha class, substantially as herein shown and described, characterized particularly as to novelty by the unusually velvety texture of the petals of its flowers, by the relatively fixed and long-lasting deep red color of its flowers, said color remaining virtually unchanged from the early bud through successive stages of bloom and enduring even under adverse weather conditions, by the long persistence of the blooms without petal deterioration, by the regularity of form of its clusters of inflorescence and their uniform production on the plant, and by the upright, compact and even growth of the plant, altogether combining to extend the usefulness and value of this variety as border and hedge plants, as well as for cut flower use and for other forms of garden decoration.

MATHIAS TANTAU.

No references cited.